(12) United States Patent
Marhold et al.

(10) Patent No.: US 6,395,921 B1
(45) Date of Patent: May 28, 2002

(54) PROCESS FOR PREPARING [BIS-(TRIFLUOROMETHYL)-PHENYL]-ACETIC ACIDS AND ALKYL ESTERS THEREOF AND DIALKYL [BIS-(TRIFLUOROMETHYL)-PHENYL]-MALONATES

(75) Inventors: Albrecht Marhold, Leverkusen; Jörn Stölting, Köln, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/635,164

(22) Filed: Aug. 9, 2000

(30) Foreign Application Priority Data

Aug. 16, 1999 (DE) .......................... 199 38 736

(51) Int. Cl.[7] .............................................. C07C 69/76
(52) U.S. Cl. .......................... 560/82; 560/83; 560/105
(58) Field of Search ............................ 560/82, 83, 105

(56) References Cited

U.S. PATENT DOCUMENTS

| 5,665,883 A | 9/1997 | Baker et al. ............... 546/210 |
| 5,696,297 A | 12/1997 | Kneuper et al. ........... 568/454 |
| 5,776,930 A | 7/1998 | Lynch, Jr. et al. ......... 514/221 |
| 5,817,658 A | 10/1998 | Siegl et al. ................. 514/221 |
| 5,817,663 A | * 10/1998 | Pees et al. |
| 5,922,906 A | * 7/1999 | Lynch et al. |

FOREIGN PATENT DOCUMENTS

| DE | 33 14 249 | 10/1984 |
| WO | 96/05827 | 2/1996 |
| WO | 98/07722 | 2/1998 |

OTHER PUBLICATIONS

Jerry March, Advanced Organic Chemistry, 4th edition, 1992.*
Lindley, James, Copper Assisted Nucleophilic Substitution of Aryl Halogen, Tetrahedron, vol. 40, No. 9, pp1456–1456, 1984.*
Aldrich , Handbook of Fine Chemicals, 1996–1997.*
Lindley, James Copper Assited Nucleophilic Substitutionv of Aryl Halogen, Tetrahedron , vol. 40, No. 9, pp1433–1456.*

* cited by examiner

Primary Examiner—Paul J. Killos
Assistant Examiner—Hector M Reyes
(74) Attorney, Agent, or Firm—Joseph C. Gil; Richard E. L. Henderson

(57) ABSTRACT

[Bis-(trifluoromethyl)-phenyl]-acetic acids are obtained in an advantageous manner by reacting an appropriate bromo- or iodo-bis-(trifluoromethyl)-benzene with a di-$C_1$-$C_4$-alkyl malonate in the presence of a deprotonating agent and a copper salt and hydrolysing and decarboxylating the reaction product in basic medium. It is possible to obtain a mixture of alkyl [bis-(trifluoromethyl)-phenyl]-acetate and alkyl [bis-(tri-fluoromethyl)-phenyl]-malonate by admixing the reaction mixture which is present before hydrolysis and complete decarboxylation with water and acid and heating. From the mixture, it is possible to obtain alkyl [bis-(trifluoromethyl)-phenyl]-acetate by distillation under reduced pressure and dialkyl [bis-(trifluoromethyl)-phenyl]-malonate by work-up by column chromatography, fractional distillation or film distillation.

[Bis-(trifluoromethyl)-phenyl]-malonic esters are novel compounds.

14 Claims, No Drawings

PROCESS FOR PREPARING [BIS-(TRIFLUOROMETHYL)-PHENYL]-ACETIC ACIDS AND ALKYL ESTERS THEREOF AND DIALKYL [BIS-(TRIFLUOROMETHYL)-PHENYL]-MALONATES

BACKGROUND OF THE INVENTION

The present invention relates to a process for preparing [bis-(trifluoromethyl)-phenyl]-acetic acids and alkyl esters thereof from bromo-bis-(trifluoromethyl)- benzenes and dialkyl malonates and to dialkyl [bis-(trifluoromethyl)-phenyl]-malonates which can be obtained as intermediates in this process.

Bis-(trifluoromethyl)-substituted phenylacetic acids and derivatives thereof are important intermediates for pharmaceutically active compounds (see, for example, U.S. Pat. No. 5,817,658, WO 98/00405, WO 98/07722, WO 95/21819 and U.S. Pat. No. 5,696,267).

WO 96/05827 describes the preparation of 2,4-bis-(trifluoromethyl)-phenylacetic acid by acid hydrolysis of the corresponding phenylacetonitrile. The yield of 68.5% is unsatisfactory. The nitrile was prepared from 2,4-bis(-trifluoromethyl)-benzyl bromide, which is difficult to obtain, by reaction with a large excess of sodium cyanide. Owing to its toxicity, the handling and disposal of the sodium cyanide requires considerable expense with respect to industrial hygiene.

Methyl 3,5-bis(trifluoromethyl)-phenylacetate can be prepared by esterification of the corresponding acid with thionyl chloride in the presence of methanol (WO 95/21819). No details are given here with respect to the synthesis of the bis-(trifluoromethyl)-phenylacetic acid structure.

The same ester can also be obtained in a yield of about 75% of theory by base hydrolysis and acid work-up from 1-β,β,β-trichloroethyl-3,5-bis-(trifluoromethyl)-benzene. This, in turn, was obtained by reaction of 3,5-bis-(trifluoromethyl)-aniline, which has been diazotized in hydrochloric acid, with vinylidene chloride in a yield of 73% (DE 33 14 249). It is generally known that the yields in this type of reaction are not reproducible and vary considerably. When this process was repeated, yields of barely 10 to barely 50% of theory were achieved. In addition, vinylidene chloride (1,1-dichloroethene) is a carcinogenic substance which can only be handled with considerable expense.

Accordingly, there continues to be a demand for a simple process for preparing [bis-(trifluoromethyl)-phenyl]-acetic acids and alkyl esters thereof in high yields requiring the handling of less toxic and noncarcinogenic substances which employs starting materials which are readily obtainable.

SUMMARY OF THE INVENTION

This invention accordingly provides a process for preparing [bis-(trifluoromethyl)-phenyl]-acetic acids, characterized in that an appropriate bromo- or iodo-bis-(trifluoromethyl)-benzene is reacted with a di-$C_1$–$C_4$-alkyl malonate in the presence of a deprotonating agent and a copper salt and the reaction product is, in basic medium, hydrolysed and decarboxylated.

DETAILED DESCRIPTION OF THE INVENTION

Suitable starting materials for the process according to the invention are, for example, bromo- or iodo-bis (trifluoromethyl)-benzenes of the formula (I)

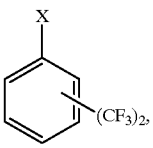

in which X represents bromine or iodine, to prepare [bis-(trifluoromethyl)-phenyl]-acetic acids of the formula (II)

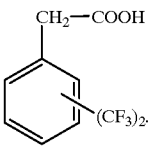

Preference is given to using bromo-bis(trifluoromethyl)-benzenes of the formula (I).

Suitable di-$C_1$–$C_4$-alkyl malonates are those of the formula (III)

in which the two radicals R are identical or different and in each case represent $C_1$–$C_4$-alkyl. The two radicals R are preferably identical and represent methyl, ethyl, n-propyl, i-propyl and n-butyl.

In the formulae (I) and (II), the two trifluoromethyl groups are preferably in the 2,4- or 3,5-position to the bromine atom and to the $CH_2$—COOH group, respectively. They are particularly preferably in the 3,5-position.

The bromo-bis(trifluoromethyl)-benzenes and di-$C_1$–$C_4$-alkyl malonates required for carrying out the process according to the invention are known and commercially available or can be prepared by known processes or analogously thereto.

Suitable deprotonating agents for the process according to the invention are inorganic and organic bases, for example alkaline earth metal and alkali metal hydrides, amides, alkoxides, carbonates and bicarbonates, such as sodium hydride, sodium amide, sodium methoxide, sodium ethoxide, potassium tert-butoxide, sodium carbonate, potassium carbonate and ammonium carbonate, sodium bicarbonate and potassium bicarbonate, and tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, 1,4-diazabicyclo [2.2.2]octane (DABCO), 1,5-diazabicyclo[5.4.0]non-5-ene (DBN) and 1,8-diazabicyclo [5.4.0]undec-7-ene (DBU). It is also possible to use combinations of different bases. Preference is given to using alkali metal alkoxides, particularly preferably the alkoxide of the alcohol R—OH in which R has the same meaning as in the di-$C_{1-C4}$-alkyl malonate employed. Alkoxides can be employed, for example, in solid form or dissolved in an alcohol, preferably in the alcohol which corresponds to the alkoxide anion.

Suitable copper salts are, for example, copper(I) salts, such as copper(I) halides. Preference is given to using copper(I) bromide or copper(I) iodide or a mixture of the two salts.

The process according to the invention can be carried out in the presence of a diluent. Suitable diluents are organic solvents which have no adverse effect on the process according to the invention, and any mixtures thereof. Examples which may be mentioned are: aromatic hydrocarbons, such as toluene, xylene and mesitylene, halogenated aromatic hydrocarbons, such as chlorobenzene and dichlorobenzenes, ethers, such as diisopropyl ether, methyl t-butyl ether, methyl t-amyl ether, dioxane, tetrahydrofuran, 1,2-dimethoxyethane, 1,2-diethoxyethane, diethylene glycol dimethyl ether and anisole, amides, such as N,N-dimethylformamide, N,N-dimethyl-acetamide, N-methylformanilide, N-methylpyrrolidine and hexamethylphosphoric triamide, N-oxides, such as N-methyl-morpholine N-oxide, esters, such as methyl acetate, ethyl acetate and butyl acetate, sulphones, such as sulpholane, and alcohols, such as methanol, ethanol, n- and i-propanol, n-, i-, s- and t-butanol, ethanediol, propane-1,2-diol, ethoxyethanol, methoxyethanol, diethylene glycol monomethyl ether and diethylene glycol monoethyl ether.

Per mole of bromo-bis-(trifluoromethyl)-benzene, it is possible to use, for example, from 1.0 to 2.5 mol, preferably from 1.1 to 1.6 mol, of di-$C_1$–$C_4$-alkyl malonate and from 0.1 to 1 mol, preferably from 0.3 to 0.5 mol, of copper salts and, if appropriate, from 0.1 to 2 1 of diluent. The deprotonating agent can be employed, for example, in an amount of from 85 to 110% of the amount which is equivalent to the malonic ester used. This amount is preferably from 90 to 99%.

The process according to the invention can be carried out, for example, at from 40 to 150° C. Preference is given to carrying out the process at from 50 to 110° C.

In a preferred embodiment of the process according to the invention, the following procedure is adopted: either the malonic ester or the deprotonating agent is initially charged, if appropriate in one of the diluents mentioned, and heated to from 40 to 70° C., and the other of the two components is metered in. Subsequently, for example when the deprotonating agent used is an alkoxide, the mixture can be subjected to incipient distillation to remove some of the alcohol formed, followed by cooling to at least some degrees below the boiling point of the distillation bottom. Copper salt and bromo-bis-(trifluoromethyl)-benzene are added, and the mixture is heated to the desired reaction temperature. If a diluent is used, the reaction temperature preferably corresponds to the reflux temperature of the diluent. During the reaction, evolution of gas can be observed which is caused by partial demethoxycarbonylation. It is also possible to adjust the reaction temperature after the addition of the copper salt and then to meter in the bromo-bis-(trifluoromethyl)-benzene, which is preferred in the case of a relatively strong evolution of gas. Essentially depending on the temperature, the reaction will generally have ended after 1 to 50 hours.

It is also possible to put aside before hand some of the copper salt, for example 5 to 30%, and to add this fraction only after some of the reaction time has already passed. Such an addition of fresh catalyst during the reaction generally leads to a reduction in the overall reaction time.

Hydrolysis and complete decarboxylation can be carried out, for example, in the following manner: to prepare [bis-(trifluoromethyl)-phenyl]-acetic acids without isolation of the intermediates, it is possible to admix the reaction mixture after the reaction and the removal of the copper salts, for example by filtration, directly with aqueous alkali, for example with 30 to 50% by weight strength aqueous sodium hydroxide solution followed by heating, for example to a temperature of at most 120° C. The product can then be isolated by customary methods, for example initially by concentration, preferably under reduced pressure, acidification of the residue with a mineral acid, such as hydrochloric acid, and isolation of the product by filtration or centrifugation. [Bis-(trifluoromethyl)-phenyl]-acetic acids can thus be obtained in yields of, for example, 85% of theory or more.

To prepare [Bis-(trifluoromethyl)-phenyl]-acetic esters without isolation of the intermediates, it is possible to adopt a different procedure after the reaction and before removal of the copper salts. Thus, it is possible to cool the mixture which is present, for example to a temperature of not less than 10° C., followed by neutralization with acid, i.e. adjusting the pH to a value in the range from 5 to 9. Suitable acids are mineral and carboxylic acids, and preference is given to acetic acid. It is then possible to separate off the solid components of the reaction mixture, for example by filtration, preferably using a filter aid, and to wash the residue with an ether or alcohol. Preference is given to using dioxane for this purpose. From the filtrate, which has been combined with the wash liquid, the product can then be obtained by distillation under reduced pressure. The distillation is preferably carried out after addition of a high-boiling inert liquid to improve heat transfer, in particular towards the end of the distillation. This work-up method is the preferred method, also for preparing (bis-[trifluoromethyl-phenyl]-acetic acids which can be obtained by customary ester hydrolysis from the corresponding esters thus isolated.

The preparation according to the invention of [bis-(trifluoromethyl)-phenyl]-acetic acids involves the corresponding dialkyl phenylmalonate and the corresponding alkyl phenylacetate intermediates. A mixture of both can be isolated by admixing the reaction mixture which is present before hydrolysis and complete decarboxylation with water and acid and heating, for example to a temperature of at most 130° C. Suitable acids are, for example, mineral and carboxylic acids. After customary work-up, for example cooling, dilution with water, extraction with organic solvent and distillation of the extract after removal of the extracting agent, a mixture can be obtained which contains the corresponding dialkyl phenylmalonate of the formula (IV) and the corresponding alkyl phenylacetate of the formula (V) and which is virtually free from the corresponding free acid of the formula (II).

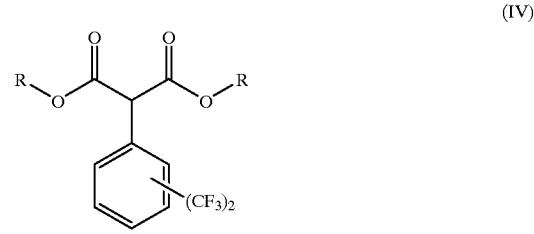

(IV)

(V)

In the formulae (IV) and (V), the radicals R have the same meaning as stated in the formula (III).

The isolated ester mixture contains more dialkyl phenylmalonate of the formula (IV) if the treatment with water and acid is only carried out for a short period of time, for example for 1 to 20 minutes, and at relatively low temperatures, for example from 10 to 30° C. Correspondingly, the isolated ester mixture contains more dialkyl phenylacetate of the formula (V) if the treatment with water and mineral acid is carried out for a relatively long period of time, for example for from 30 minutes to 5 hours, and at relatively high temperatures, for example from 30 to 130° C.

The dialkyl phenylmalonate of the formula (IV) in question can be obtained from the isolated ester mixture by work-up by, for example, column chromatography, fractional distillation or film distillation. If distillative methods are employed, the dialkyl phenylmalonate of the formula (IV) accumulates in the bottom.

The alkyl phenylacetate of the formula (V) in question can be obtained from the isolated ester mixture, for example, by distillation under reduced pressure; methyl [3,5-bis-(trifluoromethyl)-phenyl]-acetate, for example, boils at 9 mbar at from 89 to 99° C.

For example by addition of a protic solvent, for example water or alcohol, such as methanol, alkali, for example from 10 to 30% by weight strength aqueous sodium hydroxide solution, and heating to, for example, from 30 to 80° C. and acidification with a mineral acid, the corresponding phenylacetic acid of the formula (II) can be obtained from the isolated ester mixture. If this phenylacetic acid is the desired product, it is obviously not necessary to isolate the intermediate ester mixture, which would result in unnecessary expense and a reduction in yield.

The dialkyl phenylmalonates of the formula (IV) are novel. Accordingly, the present invention also relates to dialkyl [bis-(trifluoromethyl)-phenyl]-malonates of the formula (IV)

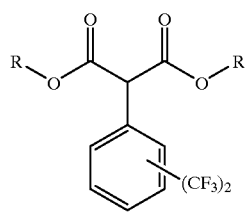

(IV)

in which the two radicals R are identical or different and in each case represent $C_1$–$C_4$-alkyl. The two radicals R are preferably identical and represent methyl, ethyl, n-propyl, i-propyl or n-butyl.

Using these malonic esters instead of the customary malonic esters, it is possible to prepare known active compounds by novel processes and to prepare novel active compounds. These malonic esters therefore represent an enrichment of the art. Arylmalonic ersters substituted in the aromatic nucleus are especially suitable for synthesizing triazolo pyrimidines which are broadly applicable fungicides in the field of agrochemicals (see EP-A 83 451).

The following examples further illustrate details for the process of this invention. The invention, which is set forth in the foregoing disclosure, is not to be limited either in spirit or scope by these examples. Those skilled in the art will readily understand that known variations of the conditions of the following procedures can be used.

EXAMPLES

Example 1

[3,5 -Bis-(trifluoromethyl)-phenyl]-acetic Acid 550 ml of ethylene glycol dimethyl ether were initially charged and, under nitrogen, 91 g of sodium methoxide (solid) were introduced, giving, without any change in temperature, a white suspension which was readily stirrable. The mixture was heated to 69° C. and 237.6 g of dimethyl malonate were added dropwise over a period of 30 minutes, during which the mixture began to boil under reflux (internal temperature 74° C.) and a stirrable white slurry was formed. After cooling to 54° C., 35.2 g of copper(I) bromide (fine powder) and 35.2 g of copper(I) iodide (fine powder) were added, and the mixture was then again heated at the boil under reflux. Over a period of 110 minutes, 344 g of 3,5-bis-(trifluoromethyl)-bromobenzene were added dropwise, and a gentle stream of waste gas was observed (partial de-methoxycarbonylation). After 15 hours and 40 minutes (conversion monitored by GC) at reflux (85° C.), a further 10 g of copper(I) bromide and a further 10 g of copper(I) iodide were added. After a further 5 hours under reflux at 86° C. (conversion monitored by GC; at least 90% conversion of the bromobenzene employed), 400 g of 45% by weight strength aqueous sodium hydroxide solution were added dropwise at 86° C. (reflux) over a period of 15 minutes and the mixture was kept at reflux at this temperature for a further 4 hours, during which a gentle evolution of waste gas took place. GC analysis then showed that no more ester was present. With stirring, 1000 ml of water were added and the precipitate was allowed to settle. Undissolved particles were then substantially decanted off over a Nutsche and the remaining content of the flask was suspended in 100 ml of 2 N aqueous sodium hydroxide solution and filtered off with suction over the Nutsche. The resulting two-phase filtrate was concentrated at 20 mbar (1350 ml of distillate) and diluted again with 1000 ml of water. Organic impurities were extracted using 30 ml of toluene (1.4 g of residue on concentration using a rotary evaporator) and the aqueous phase was poured into 920 g of 24% by weight strength aqueous sulphuric acid (18–24° C.), which resulted in strong foaming (pH=1). The resulting precipitate was filtered off with suction, washed with a little water until neutral and dried at 60° C. overnight. This gave 284 g of a beige powder, corresponding to a yield of 89% of theory.

Example 2

Methyl [3,5-bis-(trifluoromethyl)-phenyl]-acetate and Dimethyl [3,5-bis-(trifluoro-methyl)-phenyl]-malonate 2 kg of dimethyl malonate were initially charged in 6 l of dioxane at 50° C. 700 g of sodium methoxide were introduced a little at a time over a period of one hour, the reaction mixture initially turning into a paste but then once more becoming readily stirrable. After the end of the addition, the mixture was stirred at from 50 to 55° C. for 1 hour and then subjected to incipient distillation until the boiling point of dioxane (101° C.) was reached at the top (about 1 l of distillate). The reaction mixture was cooled to 90° C., 352 g each of copper(I) bromide and copper(I) iodide and 3440 g of 3,5-bis-(trifluoromethyl)-brombenzene were added and the mixture was then allowed to react under reflux for 15 hours, during which a considerable evolution of gas took place. Under reflux conditions, 2929 ml of water and 2344 ml of conc. hydrochloric acid were then introduced, and the mixture was boiled at reflux for another hour. The mixture was then cooled to room temperature, diluted with 5 l of water and extracted with tert-butyl methyl ether (2 ×with in each case 3 l). The organic phase was washed twice with 3 l of water, dried and distilled. This gave 2475 g of product which distilled over at from 91 to 125° C. and 18 mbar. The product consisted of 53% (GC, area %) dimethyl [3,5-bis- (trifluoromethyl)-phenyl]-malonate (boiling point at 10 mbar: 128° C.) and 47% (GC, area %) methyl [3,5-bis-(trifluoromethyl)-phenyl]-acetate (boiling point at 9 mbar from 89 to 99° C.).

126.2 of this product were dissolved in 4 ml of acetonitrile. 24 injections (each comprising 125 ll) of this solution were made on a RP-18 chromatographic column (corresponding to 94.7 mg of the product) and separated there. After extraction with diethylether there were obtained from the combined fractions 7.0 mg [3.5-bis-(trifluoromethyl)-phenyl]-malonate having the following characterizing data:

IR-spectrum (film, wavenumbers in cm$^{-1}$): 1744,1379, 1280, 1175, 1135, 683. mass-spectrum (GC/MS): 344 (M$^+$), 325, 300, 257, 227, 59. $^1$H-NMR-spectrum (chemical shift in ppm): 3.80 (6H), 4.77 (1H), 7.88 (1H), 7.90 (2H). $^{19}$F-NMR-spectrum (chemical shift in ppm): -63.35.

Example 3

[3,5-Bis-(trifluoromethyl)-phenyl]-acetic Acid 1 kg of the ester mixture which had been obtained according to Example 2 was initially charged in 1.5 l of methanol and, at 10° C., admixed dropwise with 2 kg of 20% by weight strength aqueous sodium hydroxide solution, the temperature increasing to about 60° C. The mixture was subsequently stirred at 60° C. for another 4 hours. The mixture was concentrated under reduced pressure, cooled and acidified with hydrochloric acid, resulting in the precipitation of the carboxylic acid. The mixture was filtered off with suction and the residue was washed with water and dried. This gave 844 g (65% of theory over the two steps) of [3,5-bis-(trifluoromethyl)-phenyl]-acetic acid of melting point 126–128° C.

Example 4

Methyl [3,5-bis-(trifluoromethyl)-phenyl]-acetate

At 69° C., 306 g of 30% by weight strength sodium methoxide solution in methanol were added dropwise over a period of 30 minutes to a mixture of 550 ml of dioxane and 287.6 g of dimethyl malonate. During the addition, the mixture began to boil at reflux, and a stirrable white slurry was formed. The mixture was then cooled to 54° C. and in each case 25.2 g of copper(I) bromide and copper(I) iodide were added as fine powders, and the mixture was once more heated at the boil at reflux. Over a period of 110 minutes, 344 g of 3,5-bis-(trifluoromethyl)-bromobenzene were added dropwise, and the mixture was stirred at unchanged temperature for 10 hours. Another 10 g each of copper(I) bromide and copper(I) iodide were then metered in, the mixture was kept at 86° C. for 5 hours, the same amounts of copper(I) bromide and copper(I) iodide were metered in again and, after another 5 hours of stirring at reflux, the mixture was cooled to room temperature. The pH was then adjusted to 7 using glacial acetic acid, the mixture was filtered through Celite®, the residue was washed with dioxane and the filtrate was combined with the wash liquid and, after addition of a high-boiling white oil, distilled at 18 mbar over a Vigreux column with attached bridge. At 18 mbar and from 91 to 125° C., the product was obtained in a yield of 52% of theory.

The corresponding acid can be obtained from the isolated ester by customary ester hydrolysis.

What is claimed is:

1. A process for preparing a [bis(trifluoromethyl)phenyl] acetic acid comprising (a) reacting a bromo- or iodo-bis(trifluoromethyl)benzene with a di(C$_1$–C$_4$-alkyl) malonate in the presence of a deprotonating agent and a copper salt, optionally in the presence of a diluent, and (b) hydrolyzing and decarboxylating the reaction product formed in step (a) in basic medium to form the [bis (trifluoromethyl)phenyl]acetic acid.

2. The process of claim 1 for preparing a [bis (trifluoromethyl)phenyl]-acetic acid having the formula (II)

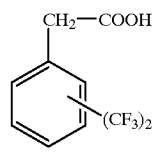

(II)

wherein (i) the bromo- or iodo-bis(trifluoromethyl)benzene has the formula (I)

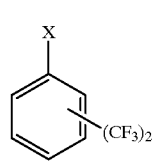

(I)

wherein X represents bromine or iodine, and (ii) the di(C$_1$–C$_4$-alkyl) malonate has the formula (III)

(III)

wherein the radicals R are identical or different and represent C$_1$–C$_4$-alkyl.

3. The process of claim 2 wherein the two trifluoromethyl groups are in the 2,4- or 3,5-position relative to a bromine atom in formula (I) and relative to CH$_2$—COOH group in formula (II).

4. The process of claim 1 wherein the deprotonating agent is selected from the group consisting of alkaline earth metals, alkali metal hydrides, amides, alkoxides, carbonates, and bicarbonates, ammonium carbonate, and tertiary amines.

5. The process of claim 1 wherein the deprotonating agent is sodium carbonate, potassium carbonate, sodium bicarbonate, or potassium bicarbonate.

6. The process of claim 1 wherein the deprotonating agent is an alkoxide in solid form.

7. The process of claim 1 wherein the deprotonating agent is an alkoxide dissolved in an alcohol.

8. The process of claim 1 wherein the copper salts are copper(I) salts.

9. The process of claim 1 wherein the diluent is a solvent selected from the group consisting of aromatic hydrocarbons, halogenated aromatic hydrocarbons, ethers, amides, N-oxides, esters, sulphones, and alcohols.

10. A process for preparing a [bis(trifluoromethyl)phenyl] acetic ester comprising (a) reacting a bromo- or iodo-bis(trifluoromethyl)benzene with a di(C$_1$–C$_4$-alkyl) malonate in the presence of a deprotonating agent and a copper salt, optionally in the presence of a diluent, (b) cooling the reaction mixture to a temperature of not less than 10° C., (c) adjusting the pH of the cooled reaction mixture to a value in the range from 5 to 9 using an acid, (d) separating off solid components remaining after step (c) to obtain a filtrate, washing the separated solid components with an ether or alcohol, and combining the filtrate and the wash liquid, (e) distilling the combined filtrate and wash liquid under reduced pressure to obtain the [bis(trifluoromethyl) phenyl]acetic ester.

11. A process for preparing a mixture of esters having the formulas (IV) and (V)

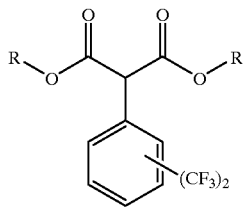

(IV)

and

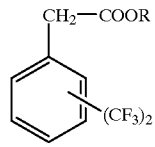

(V)

wherein radicals R are identical or different and represent $C_1$–$C_4$-alkyl, comprising (a) reacting a bromo- or iodo-bis(trifluoromethyl) benzene with a di($C_1$–$C_4$-alkyl) malonate in the presence of a deprotonating agent and a copper salt, optionally in the presence of a diluent, thereby forming a mixture containing esters having the formulas (IV) and (V), (b) admixing the ester-containing mixture with water and an acid, (c) heating the acidified aqueous mixture, and (d) working up the heated mixture by extraction and distillation to obtain a mixture of esters having the formulas (IV) and (V).

12. A process for preparing a dialkyl phenylmalonate having the formula (IV)

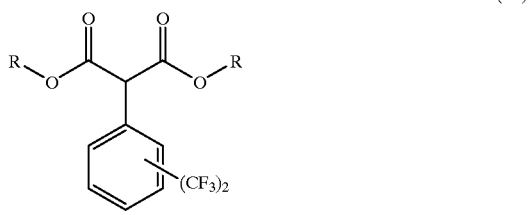

(IV)

wherein radicals R are identical or different and represent $C_1$–$C_4$-alkyl, comprising further working up a mixture of esters prepared according to claim 11 using column chromatography, fractional distillation, or film distillation.

13. A process for preparing an alkyl phenylacetates having the formula (V)

(V)

wherein R represents $C_1$–$C_4$-alkyl, comprising further working up a mixture of esters prepared according to claim 11 using distillation under reduced pressure.

14. A dialkyl [3,5-bis(trifluoromethyl)phenyl]malonate having the formula

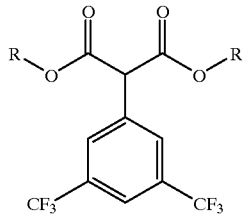

wherein the two radicals R are identical or different and represent $C_1$–$C_4$-alkyl.

* * * * *